(12) United States Patent
Kayano et al.

(10) Patent No.: US 8,183,049 B2
(45) Date of Patent: May 22, 2012

(54) METHOD FOR DETECTING LEAD PRESENT IN SPECIMEN

(75) Inventors: Kengo Kayano, Toyota (JP); Naoki Sato, Toyota (JP); Shinichiro Hirayama, Toyota (JP)

(73) Assignee: Toyota Jidosha Kabushiki Kaisha, Aichi (JP)

( * ) Notice: Subject to any disclaimer, the term of this patent is extended or adjusted under 35 U.S.C. 154(b) by 0 days.

(21) Appl. No.: 13/121,110

(22) PCT Filed: Oct. 30, 2008

(86) PCT No.: PCT/JP2008/069748
§ 371 (c)(1),
(2), (4) Date: Mar. 25, 2011

(87) PCT Pub. No.: WO2010/050026
PCT Pub. Date: May 6, 2010

(65) Prior Publication Data
US 2011/0177604 A1    Jul. 21, 2011

(51) Int. Cl.
*G01N 33/20* (2006.01)
(52) U.S. Cl. ............ 436/77; 436/73; 436/135; 436/164; 436/166; 436/169; 422/400; 422/420; 422/406; 422/411; 422/418
(58) Field of Classification Search .................... 436/73, 436/77, 135, 164, 166, 169; 422/400, 406, 422/408, 411, 418, 420
See application file for complete search history.

(56) References Cited

U.S. PATENT DOCUMENTS

| | | | |
|---|---|---|---|
| 5,039,618 A * | 8/1991 | Stone | 436/77 |
| 5,278,075 A * | 1/1994 | Stone | 436/73 |
| 5,330,917 A * | 7/1994 | Stone | 436/73 |
| 5,364,792 A * | 11/1994 | Stone | 436/73 |
| 5,416,028 A * | 5/1995 | Stone | 436/77 |
| 5,567,619 A * | 10/1996 | Stone | 436/77 |
| 6,225,128 B1 * | 5/2001 | White | 436/77 |
| 6,248,593 B1 | 6/2001 | Esswein et al. | |
| 6,800,485 B2 * | 10/2004 | Cole | 436/77 |
| 2005/0285274 A1 | 12/2005 | Burnette et al. | |

FOREIGN PATENT DOCUMENTS

| | | |
|---|---|---|
| JP | 2002-511929 A | 4/2002 |
| JP | 2008-504963 A | 2/2008 |
| WO | 98/57167 A1 | 12/1998 |

OTHER PUBLICATIONS

John H. Gould, et al.,"A Quick Color Test to Detect Lead Release from Glazed Ceramic and Enameled Metalware", Analytical Letters, 1988, pp. 2145-2154, vol. 21, No. 11.
A.M.Beale, et al., "A Rapid Lead Test: Public Outreach and Testing to Detect Leachable Lead in Ceramic Ware", Archives of Environmental Contamination and Toxicology, 1991, pp. 423-426, vol. 20.
Herbert Weisz, et al., "Variations of the Segment Technique in the Ring Oven Method", Mikrochimica Acta, 1982, pp. 289-295, vol. 2, No. 3-4.
Ervin Jungreis, et al.; "A Simple Direct Estimation of Ultramicroquantities of Lead in Drinking Water Using Sodium Rhodizonate", Microchemical Journal, 1986, pp. 219-221, vol. 34, No. 2.
James R. Preer, et al., "A Simplified Method for Detection of Lead Contamination of Soil", Environmental Pollution Series B, 1986, pp. 1-13, vol. 12, No. 1.

* cited by examiner

*Primary Examiner* — Maureen Wallenhorst
(74) *Attorney, Agent, or Firm* — Sughrue Mion, PLLC

(57) ABSTRACT

With respect to a lead detection method that uses rhodizonic acid, it is made possible to clearly identify pink or red coloration caused by a reaction between lead and rhodizonic acid even in cases where Sn is present in a specimen. To this end, an acidic aqueous solution or a buffer solution thereof (e.g., tartaric acid) in which hydrogen peroxide coexists is used as a reagent. Hydrogen peroxide oxidizes $Sn^{2+}$ into $Sn^{4+}$. Since $Sn^{4+}$ does not react with rhodizonic acid, the presence of Sn does not interfere with the visual identification of any pink or red coloration caused by the reaction between lead and rhodizonic acid.

6 Claims, No Drawings

METHOD FOR DETECTING LEAD PRESENT IN SPECIMEN

CROSS REFERENCE TO RELATED APPLICATION

This application is a National Stage of International Application No. PCT/JP2008/069748 filed Oct. 30, 2008, the contents of all of which are incorporated herein by reference in their entirety.

TECHNICAL FIELD

The present invention relates to a method for detecting lead present in a specimen, and more particularly to, although by no means limited as such, a lead detection method that is suitable for detecting whether or not lead is present in an electronic component for which there is a strong possibility that plating or solder containing Sn is used.

BACKGROUND ART

Given that lead is detrimental to the human body and could cause environmental pollution, it is demanded in many fields that the use of lead be stopped. For example, in Europe, there are restrictions on lead use in in-vehicle electronic components. With respect to mechanical components and the like, it is often difficult to visually determine whether or not lead is used in parts thereof. Thus, detection methods have been proposed where easy visual detection of lead is made possible by way of chemical reactions. For example, a lead testing kit based on the lead and rhodizonate ion reaction system is available from HybrilVet Systems, Inc. of the United States under the brand "Lead Check(trademark)." In this kit, two types of reagents (sodium rhodizonate and a tartrate buffer) are used. The surface to be tested is rubbed with the tip of a swab saturated with the mixed reagents. By observing for a change in the color of the swab tip caused thereby, the presence of lead is detected. A color change to pink or red indicates the presence of lead, and the lack of any color change indicates the absence of significant levels of lead.

As another example, Patent Document 1 discloses, as a lead detection method suitable for the detection of lead contamination present on the surface of human skin, a method for detecting the presence of lead, comprising: wiping with a handwipe the surface (skin) suspected of lead contamination; solubilizing any lead collected on the handwipe with an acidic aqueous solution; and then treating the solubilized lead ions with rhodizonate ions.

Patent Document 1: WO 98/57167

DISCLOSURE OF THE INVENTION

Problems to be Solved by the Invention

In such electronic components as, for example, semiconductor devices in which an IC chip is mounted on a leadframe, which are widely in use as in-vehicle electronic components, brass, copper alloys, alloy 42 (Fe-42 wt % Ni) and the like are used for the base material of terminals. However, with the base material left as is, the terminal surface may oxidize and cause faulty conduction due to faulty soldering and the like. Therefore, ordinarily, a protective film is formed on the surface of the terminal by plating and the like. For the material of the plating layer, Sn or Sn alloys are generally used. A plating solution containing lead (Pb) is sometimes used as well. In addition, an alloy chiefly composed of lead and Sn is used for the solder to be used as well in some cases.

From the perspective of alleviating the burden on the environment, turning lead-free is being called for in recent years. For example, the use of plating solutions that do not contain lead is being called for. In addition, the use of so-called lead-free solder, such as Sn and Sn—Ag alloys that do not contain lead, is being called for.

Thus, with respect to in-vehicle electronic components and the like, there is a need for a lead detection method that is capable of quickly and accurately detecting whether or not lead is used therein, which the above-mentioned detection method using rhodizonic acid is unable to adequately cater to.

The reason for this is that while there is a strong possibility that Sn is present in the plating layer and the solder layer on the surface of an in-vehicle electronic component as mentioned above, rhodizonate ions react with $Sn^{2+}$ ions, which are produced as Sn solubilizes, as well to produce a purple precipitate. Consequently, a purple color is exhibited, and even if, in cases where lead is present, the rhodizonate ions were to react with the lead ions to result in a pink or red color, it would be difficult to visually identify the pink or red color that is produced. In addition, if Sn is present in high concentration, there may be cases where the reaction with the $Sn^{2+}$ ions would precede, and lead would not be detectable.

The present invention seeks to solve the above-mentioned inconveniences, where a problem and an object thereof are to disclose a novel lead detection method that uses rhodizonic acid and that is capable of reliably detecting the presence of lead even in such cases where Sn is present on the surface of a specimen.

Means for Solving the Problems

In order to solve the problem above, the present inventors, through extensive experimentation, found that rhodizonic acid, while exhibiting color by reacting with $Sn^{2+}$ ions, does not react with $Sn^{4+}$ ions, and no color is produced through any reaction. The present invention is made based on the finding above obtained by the present inventors.

A first invention is a method for detecting lead present in a specimen, the lead detection method comprising at least: a step of bringing the specimen into contact with an acidic aqueous solution or a buffer solution thereof and with a hydrogen peroxide solution; and a step of thereafter bringing the specimen into contact with an aqueous solution of rhodizonic acid or of a rhodizonic acid salt.

In the first invention, the step of bringing the specimen into contact with the acidic aqueous solution or the buffer solution thereof and with the hydrogen peroxide solution may also be performed by bringing a mixed solution of the acidic aqueous solution or the buffer solution thereof and the hydrogen peroxide solution into contact with the specimen. Alternatively, the step may also be performed in two steps, namely, a step of bringing the acidic aqueous solution or the buffer solution thereof into contact with the specimen, and a step of bringing the hydrogen peroxide solution into contact with the specimen.

A second invention is a method for detecting lead present in a specimen, the lead detection method comprising at least: a step of impregnating the tip of a stick member with a mixed solution of an acidic aqueous solution or a buffer solution thereof and a hydrogen peroxide solution; a step of rubbing the tip portion of the stick member impregnated with the mixed solution over a surface of the specimen; and a step of dripping an aqueous solution of rhodizonic acid or of a rhodizonic acid salt on the tip of the stick member after the rubbing.

A third invention is a method for detecting lead present in a specimen, the lead detection method comprising at least a step of impregnating the tip of a stick member with an acidic aqueous solution or a buffer solution thereof; a step of rubbing the tip portion of the stick member impregnated with the acidic aqueous solution or the buffer solution thereof over a surface of the specimen; a step of dripping a hydrogen peroxide solution on the tip of the stick member after the rubbing; and a step of dripping an aqueous solution of rhodizonic acid or of a rhodizonic acid salt on the tip of the stick member after dripping of the hydrogen peroxide solution.

BEST MODE FOR CARRYING OUT THE INVENTION

In the methods for detecting lead present in a specimen according to the respective inventions in the present application, there is included as a requisite step the bringing of a substance present on a surface of the specimen into contact with a hydrogen peroxide solution. In a subsequent step, the portion of the specimen that has been in contact with hydrogen peroxide is brought into contact with an aqueous solution of rhodizonic acid or of a rhodizonic acid salt.

If Sn is present on the surface of the specimen, $Sn^{2+}$ ions that are produced as Sn is solubilized are oxidized by hydrogen peroxide to become $Sn^{4+}$ ions. Since $Sn^{4+}$ ions do not react with rhodizonic acid, even if Sn were present, no significant color would be exhibited in connection therewith. It thus becomes possible to reliably identify visually the pink or red color exhibited as rhodizonate ions react with lead ions when lead is present.

The concentration of the hydrogen peroxide solution should preferably be 0.1-10 wt %. At below 0.1 wt %, when Sn is present, there may occur cases where not all of it would be oxidized into $Sn^{4+}$ ions. In such cases, coloration would be caused due to a reaction between Sn and rhodizonic acid, which is undesirable since it would become difficult to visually identify any coloration caused by a reaction between lead and rhodizonic acid. In addition, once 10 wt % is exceeded, rhodizonic acid would be oxidized by hydrogen peroxide and, consequently, the reaction between rhodizonic acid and lead would not proceed, which is undesirable as there would a tendency for the coloration to be pale even when lead is present.

In the lead detection methods according to the respective inventions in the present application, the acidic aqueous solution facilitates the solubilization of lead. Thus, it is made easier for rhodizonate ions to react with $Pb^+$ ions. While any acid may be used, examples may include such inorganic acids as hydrochloric acid, sulfuric acid, nitric acid and the like, or such organic acids as acetic acid, citric acid, tartaric acid, and the like. It may be an acid or salts thereof, and a buffer solution thereof may also be used. The concentration of the acid, in pH, should preferably be within 1-5. At a pH of less than 1, rhodizonic acid and lead do not produce chelate compounds, and no coloration reaction would occur. Consequently, sufficient coloration may sometimes not be obtained even though lead is present. At pHs exceeding 5, the dissolving power of lead drops, and sufficient coloration, again, would not be obtained.

In all of the lead detection methods in the present application, for the rhodizonic acid to be used, rhodizonic acid or rhodizonic acid salts used in conventional lead detection methods that use rhodizonic acid can be used without modification. Examples include sodium rhodizonate, potassium rhodizonate, disodium rhodizonate, or dipotassium rhodizonate. They may be aqueous solutions and they may also be buffered solutions thereof.

As for the amount of rhodizonic acid, there need only be rhodizonate ions of an amount that would exhibit visible coloration upon reaction with the solubilized lead. For an aqueous solution, there should preferably be contained 0.05-0.5 wt % of rhodizonic acid or a salt thereof. At below 0.05 wt %, the coloration from the reaction with lead would become pale, making visible identification difficult. At above 0.5 wt %, saturation would occur, there would be undissolved residues, and it would be excessive.

Each of the lead detection methods according to the present invention is applicable to any given specimen, but, as discussed above, is particularly suitable for application to specimens for which there is a strong possibility that Sn is present, an example of which may include electronic components. It is noted that there is a strong possibility that the plating or solder applied to electronic components contains Ag in addition to Sn. However, since Ag has a smaller ionization tendency and is less soluble, it does not interfere with the detection of lead in the respective lead detection methods according to the present invention. However, as rhodizonic acid produces colored compounds with $Ag^+$, $Sn^{2+}$, $Ba^{2+}$, $Sr^{2+}$, $Cd^{2+}$, and $Tl^+$, there may be cases where sufficient coloration will not occur if the specimen is such that any one of $Ba^{2+}$, $Sr^{2+}$, $Cd^{2+}$, and $Tl^+$ coexists with lead.

In a lead detection method according to the present invention, an acidic aqueous solution or a buffer solution thereof and a hydrogen peroxide solution may be applied to a surface of a specimen, and, after a predetermined period, an aqueous solution of rhodizonic acid or of a rhodizonic acid salt may be applied to at least the area where the hydrogen peroxide solution was applied. In this case, too, if pink or red coloration is observed, it can be determined that the presence of lead has been detected, and if no pink or red coloration is observed, it can be determined that the presence of lead is not detected. Further, the presence of Sn does not interfere with the pink or red coloration.

The method above is unsuitable for detecting the presence/absence of lead in a small area, such as a connection terminal of an electronic component, such as a semiconductor device. This is because the acidic aqueous solution, hydrogen peroxide, and rhodizonic acid as reagents may go beyond the area to be tested and spread to other areas, thereby causing defects in the specimen.

In seeking to detect the presence/absence of lead in an electronic component such as a semiconductor device, an embodiment is recommended where there is used a stick member, whose tip is impregnated with a mixed solution of an acidic aqueous solution or a buffer solution thereof and a hydrogen peroxide solution. In this embodiment, the portion to be tested is rubbed with the tip of the stick member that is impregnated with the mixed solution. Thus, a part of the surface of the portion to be tested and the solubilized lead are transferred to the tip of the stick member. The Sn that is contained in the part of the surface of the portion to be tested that has been transferred reacts with hydrogen peroxide to become $Sn^{4+}$ ions. Then, as the aqueous solution of rhodizonic acid or of a rhodizonic acid salt is dripped on the tip of the stick member, the tip would exhibit a pink or red color if lead is present, and there would be no change in color if no lead is present.

With this embodiment, by selecting a shape for the tip of the stick member as deemed appropriate, there are such advantages as being able to obtain a sample from an extremely small area, as well as being able to minimize damage to the specimen due to the reagents.

As a variation of this embodiment, the surface of the specimen may be rubbed with the tip of a stick member, the tip being impregnated only with an acidic aqueous solution or a buffer solution thereof, and a hydrogen peroxide solution may be dripped on the tip of the stick member after the rubbing. The same advantages as those above can be attained through this embodiment as well.

In experiments by the present inventors, in the case of a detection method using a stick member, it was possible to clearly detect the presence/absence of lead even when the area to be detected was a plated portion of a minute area (for example, one lead of an IC chip, approximately 0.05 cm$^2$) containing 10 wt % of lead. Further, since a mixed solution wherein a hydrogen peroxide solution is dripped into an acidic aqueous solution or a buffer solution thereof (in particular, a tartaric acid aqueous solution or a buffer solution thereof) is oxygen-rich, there was observed a tendency where lead solubilization was promoted more than in the case of the acidic aqueous solution or the buffer solution thereof alone. Consequently, regardless of the presence/absence of Sn, it was possible to detect the presence of extremely small amounts, namely, approximately 0.1 μm, of lead through a method of the present invention.

EXAMPLES

Example 1

Step 1: A stick member with an unwoven fabric attached to a tip face of a paper shaft was used. As a reagent, a mixed solution was prepared where 7 mL of a 30% hydrogen peroxide solution was added to 93 mL of a tartrate buffer solution of a 2.8 pH (the hydrogen peroxide concentration being approximately 2 wt %). The tip of the stick member was dipped in the reagent, and the tip was thus impregnated with approximately 0.01 mL of the reagent. Any excessive reagent adhered to the tip of the stick member was then removed.

Step 2: The tip of the stick member impregnated with the reagent was rubbed over the surface of a specimen, on the surface of which lead and Sn were present, for approximately 10 seconds. In addition to the lead solubilizing action by tartaric acid, due to the rubbing with the tip of the stick member, a part of the surface containing Sn and the solubilized lead were transferred to the tip of the stick member.

Step 3: A 0.2 wt % disodium rhodizonate aqueous solution prepared immediately before use was dripped on the tip of the stick member. As the rhodizonic acid aqueous solution is dark yellow in color and interferes with the identification of any coloration by lead, any excessive rhodizonic acid aqueous solution present in the surroundings was removed.

Step 4: The area where the rhodizonic acid aqueous solution was dripped was observed. It was visually identified that the area exhibited a pink color.

Example 2

Step 1: A stick member with an unwoven fabric attached to a tip face of a paper shaft was used. As a reagent, 93 mL of a tartrate buffer solution of a 2.8 pH was used. The tip of the stick member was dipped in the reagent, and the tip was thus impregnated with approximately 0.01 mL, of the reagent. Any excessive reagent adhered to the tip of the stick member was then removed.

Step 2: The tip of the stick member impregnated with the reagent was rubbed over the surface of a specimen, on the surface of which lead and Pb were present, for approximately 10 seconds. In addition to the lead solubilizing action by tartaric acid, due to the rubbing with the tip of the stick member, a part of the surface containing Sn and the solubilized lead were transferred to the tip of the stick member.

Step 3: A hydrogen peroxide solution with a concentration of approximately 2 wt % was dripped on the tip of the stick member.

Step 4: A 0.2 wt % disodium rhodizonate aqueous solution prepared immediately before use was dripped on the tip area of the stick member where the hydrogen peroxide solution was dripped. As the rhodizonate aqueous solution is dark yellow in color and interferes with the identification of any coloration by lead, any excessive rhodizonate aqueous solution present in the surroundings was removed.

Step 5: The area where the rhodizonate aqueous solution was dripped was observed. It was visually identified that the area exhibited a pink color.

Comparative Example 1

An experiment was conducted in a similar fashion to Example 1 except for the fact that 93 mL of a tartrate buffer solution of a 2.8 pH was used as a reagent. The tip of the stick member was observed for any change in color. The whole of it exhibited a purple color, and no pink coloration could be visually identified clearly.

Discussion

In Examples 1 and 2, by virtue of the coexistence of hydrogen peroxide within the reagent, Sn that was present at the tip of the stick member changed from $Sn^{2+}$ ions to $Sn^{4+}$ ions. It is speculated that it was possible to visually identify clearly the pink coloration caused by the reaction between lead and rhodizonic acid because $Sn^{4+}$ does not react with rhodizonic acid. On the other hand, it is speculated that, since the reagent did not contain hydrogen peroxide in Comparative Example 1, the $Sn^{2+}$ ions present at the tip of the stick member reacted with rhodizonic acid to exhibit purple coloration, thereby making it impossible to visually identify clearly any pink coloration caused by the reaction between lead and rhodizonic acid.

The invention claimed is:

1. A method for detecting lead present in a specimen, comprising at least:
   a step of bringing the specimen into contact with a mixed solution comprising an acidic aqueous solution or a buffer solution thereof and a hydrogen peroxide solution; and
   a step of then bringing the specimen into contact with an aqueous solution of rhodizonic acid or of a rhodizonic acid salt.

2. The lead detection method according to claim 1, wherein the acidic aqueous solution or the buffer solution is an aqueous solution of or a buffer solution of an organic acids selected from tartaric acid, citric acid, acetic acid, or of an inorganic acid, wherein the inorganic acid is nitric acid, and has a pH within 1 to 5.

3. The lead detection method according to claim 1, wherein the rhodizonic acid salt is one of sodium rhodizonate, potassium rhodizonate, disodium rhodizonate, and dipotassium rhodizonate.

4. The lead detection method according to claim 1, wherein the specimen is an electronic component.

5. A method for detecting lead present in a specimen, comprising at least:
   a step of impregnating a tip of a stick member with a mixed solution of an acidic aqueous solution or a buffer solution thereof and a hydrogen peroxide solution;

a step of rubbing the tip of the stick member impregnated with the mixed solution over a surface of the specimen; and a step of dripping an aqueous solution of rhodizonic acid or of a rhodizonic acid salt on the tip of the stick member after the rubbing.

6. A method for detecting lead present in a specimen, comprising at least:

a step of impregnating a tip of a stick member with an acidic aqueous solution or a buffer solution thereof;

a step of rubbing the tip of the stick member impregnated with the acidic aqueous solution or the buffer solution thereof over a surface of the specimen;

a step of dripping a hydrogen peroxide solution on the tip of the stick member after the rubbing; and a step of dripping an aqueous solution of rhodizonic acid or of a rhodizonic acid salt on the tip of the stick member after the dripping of the hydrogen peroxide solution.

* * * * *